United States Patent
Katou et al.

(10) Patent No.: US 11,312,933 B2
(45) Date of Patent: Apr. 26, 2022

(54) SET FOR TRANSPORTING CULTURE CONTAINER AND UNIT FOR TRANSPORTING CELL OR BIOLOGICAL TISSUE

(71) Applicant: SANPLATEC CORPORATION LTD., Osaka (JP)

(72) Inventors: Satoshi Katou, Osaka (JP); Junichi Kuwabara, Osaka (JP); Hidenori Nakajima, Kyoto (JP); Yoshifumi Kobayashi, Kyoto (JP)

(73) Assignee: SANPLATEC CORPORATION LTD., Osaka (JP)

( * ) Notice: Subject to any disclaimer, the term of this patent is extended or adjusted under 35 U.S.C. 154(b) by 231 days.

(21) Appl. No.: 16/313,372

(22) PCT Filed: Jun. 30, 2016

(86) PCT No.: PCT/JP2016/069487
§ 371 (c)(1),
(2) Date: Dec. 26, 2018

(87) PCT Pub. No.: WO2018/003073
PCT Pub. Date: Jan. 4, 2018

(65) Prior Publication Data
US 2019/0225926 A1 Jul. 25, 2019

(51) Int. Cl.
*C12M 1/00* (2006.01)
*C12M 3/00* (2006.01)
(Continued)

(52) U.S. Cl.
CPC ............ *C12M 23/52* (2013.01); *C12M 23/24* (2013.01); *C12M 23/36* (2013.01); *C12M 23/38* (2013.01);
(Continued)

(58) Field of Classification Search
CPC .............................. C12M 45/22; C12M 23/38
See application file for complete search history.

(56) References Cited

U.S. PATENT DOCUMENTS

| 6,670,174 B1* | 12/2003 | Smith ............... C12M 23/10 |
| | | 435/303.2 |
| 2007/0212750 A1* | 9/2007 | Kieffer .............. C12M 29/04 |
| | | 435/34 |

(Continued)

FOREIGN PATENT DOCUMENTS

| JP | 2002-159284 | 6/2002 |
| JP | 2007-284137 | 11/2007 |

(Continued)

OTHER PUBLICATIONS

International Search Report, issued in the corresponding PCT application No. PCT/JP2016/069487, dated Sep. 27, 2016, 5 pages.

*Primary Examiner* — Jonathan M Hurst
(74) *Attorney, Agent, or Firm* — Hamre, Schumann, Mueller & Larson, P.C.

(57) ABSTRACT

A culture container transportation set suitable for cultured state-maintaining transportation is provided. A culture container transportation set A1 includes: a culture container 13 including a vessel 13 made up of a bottom wall 11 and a tubular side wall 12 rising from the bottom wall 11; a flexible cover 2 covering an upper edge portion 121 of the side wall 12; a hard pressing member 3 provided on the cover 2; a cushioning material 4 of shape restorability; and a housing container 6 that houses the culture container 1, the cover 2, the pressing member 3 and the cushioning material 4 in an assembled state in which these components are stacked while pressing these components from above and below. The cushioning material 4 is provided between the (Continued)

housing container 6 and the culture container 1 or between the pressing member 3 and the housing container 6.

15 Claims, 13 Drawing Sheets

(51) Int. Cl.
    *C12M 1/107*         (2006.01)
    *C12M 1/04*           (2006.01)

(52) U.S. Cl.
    CPC ............ C12M 23/54 (2013.01); C12M 29/26 (2013.01); C12M 45/22 (2013.01)

(56) References Cited

U.S. PATENT DOCUMENTS

| | | | |
|---|---|---|---|
| 2007/0245763 A1 | 10/2007 | Uchida et al. | |
| 2010/0062528 A1 | 3/2010 | Chesne | |
| 2010/0079751 A1* | 4/2010 | Porat | B01L 3/502 356/300 |
| 2012/0282690 A1 | 11/2012 | Oura et al. | |
| 2014/0302602 A1 | 10/2014 | Kawasaki | |

FOREIGN PATENT DOCUMENTS

| | | |
|---|---|---|
| JP | 2010-503390 | 2/2010 |
| JP | 2013-039103 | 2/2013 |
| JP | 2013-048567 | 3/2013 |
| JP | 2013-128457 | 7/2013 |
| JP | 2015-002721 | 1/2015 |
| WO | 2011/065363 | 6/2011 |
| WO | 2013/094370 | 6/2013 |

\* cited by examiner

SET FOR TRANSPORTING CULTURE CONTAINER AND UNIT FOR TRANSPORTING CELL OR BIOLOGICAL TISSUE

TECHNICAL FIELD

The present invention relates to a technology for transporting cells or biological tissues while maintaining the cultured state of the cells or the biological tissues, and particularly to a technology of transportation using culture containers commonly used in research fields.

BACKGROUND ART

Culture containers such as petri dishes (receivers), well plates, and probes are widely used to culture cells or a biological tissue. These culture containers are designed for culture under ventilated conditions. Accordingly, even if such a culture container has a lid, the lid is designed so as to be merely placed on the culture container and cannot seal the culture container. A method commonly employed to seal the culture container is, for example, to attach a film with adhesive to an upper edge portion of the tubular wall of the container. Also, covering the upper edge portion of the tubular wall of the container using an elastomer sheet as a lid has been proposed (see Patent Document 1, for example).

When culturing cells, cultured cells proliferate in a state of being covered with the required amount of a culture medium in the culture container. Conventionally, it is often the case that cultured cells are frozen when transported. When cultured cells are transported in a frozen state, the cultured cells are transferred from a culture container to a dedicated container for cryopreservation, frozen, and then transported. Thereafter, the cultured cells are thawed and transferred again to a culture container containing the required amount of a culture medium. This may involve the risk of contamination and a loss of cells due to the cells being transferred between containers, and there is the issue that it takes a long period of time and various types of technologies such as those of freezing and thawing are needed in order to enable use of the cells. In recent years, owing to progress in constant-temperature transportation technology, cells can be transported without being frozen while maintaining a temperature suitable for culture. Transporting cells while maintaining the cultured state thereof makes it possible to use the cells for experiments, studies, and the like immediately after the cells reach a destination.

In the case where an opening of the culture container is closed using the above-described film with adhesive for transportation of the culture container, although the culture container may be sealed, the culture medium may come into direct contact with the adhesive surface of the film. Accordingly, there is a risk of contamination resulting from elution of the adhesive. In addition, the contents of the culture container may spill out of the container in reaction to the action of removing the adhesive film. The method of covering the container using the elastomer sheet as a lid does not achieve sufficiently reliable liquid sealing performance during the transportation.

PRIOR ART DOCUMENTS

Patent Document

Patent Document 1: JP 2002-159284A

SUMMARY OF THE INVENTION

Problem to be Solved by the Invention

The present invention was devised in light of the above-described circumstances, and a main object of the present invention is to provide a culture container transportation set suitable for cultured state-maintaining transportation.

Means for Solving the Problem

In order to solve the above-described problems, the present invention employs the following technical solutions.

A first aspect of the present invention provides a culture container transportation set including: a culture container including at least one vessel made up of a bottom wall and a tubular side wall that rises from the bottom wall; a flexible cover that covers an upper edge portion of the side wall; a hard pressing member that is provided on the cover; a cushioning material having shape restorability; and a housing container that houses the culture container, the cover, the pressing member and the cushioning material in an assembled state in which these components are stacked while pressing these components from above and below. The cushioning material is provided between the housing container and the culture container or between the pressing member and the housing container.

In a preferred embodiment, the cover has a gas-permeable portion at a position located inside the side wall as viewed in a vertical direction.

In a preferred embodiment, the cover includes a thick portion that is in intimate contact with the upper edge portion of the side wall and has a relatively large thickness, and a gas-permeable thin portion that is surrounded by the thick portion as viewed in the vertical direction and has a relatively small thickness.

In a preferred embodiment, the thick portion has resealing properties with which a hole formed by piercing the thick portion with an injection needle is closed, and is in intimate contact with a lower surface of the pressing member in the assembled state.

In a preferred embodiment, the cover includes a protruding portion that is accommodated inside the side wall and protrudes toward the bottom wall.

In a preferred embodiment, the cover is formed of a gas-permeable film.

In a preferred embodiment, the pressing member includes a tubular portion that is accommodated inside the side wall and extends downward toward the bottom wall.

In a preferred embodiment, the pressing member is formed with a through hole that is located inside the side wall as viewed in the vertical direction and passes through the pressing member in the vertical direction.

In a preferred embodiment, the housing container includes a base member having a housing portion made up of a bottom plate and a side plate that rises from the bottom plate, a lid body for closing an opening of the base member, and a ring-shaped packing member formed of a flexible material. At least one of the base member and the lid body is provided with a locking device that prevents relative movement between the base member and the lid body in a state in which the packing member is sandwiched between the base member and the lid body.

In a preferred embodiment, the housing container forms an inner space sealed off from the outside.

A preferred embodiment further includes an atmosphere conditioning agent for adjusting a gas concentration inside the housing container.

In a preferred embodiment, the atmosphere conditioning agent contains ascorbic acids and adjusts an oxygen concentration and a carbon dioxide concentration.

In a preferred embodiment, the cushioning material is a net body.

A second aspect of the present invention provides a cell and biological tissue transportation unit including: a culture container transportation set according to the first aspect of the present invention; and cells or biological tissues placed in the vessel of the culture container transportation set together with a culture medium.

Other characteristics and advantages of the present invention will become more apparent by the following detailed description with reference to the accompanying drawings.

MODE FOR CARRYING OUT THE INVENTION

Hereinafter, preferred embodiments of the present invention will be described with reference to the drawings.

Figure 1:
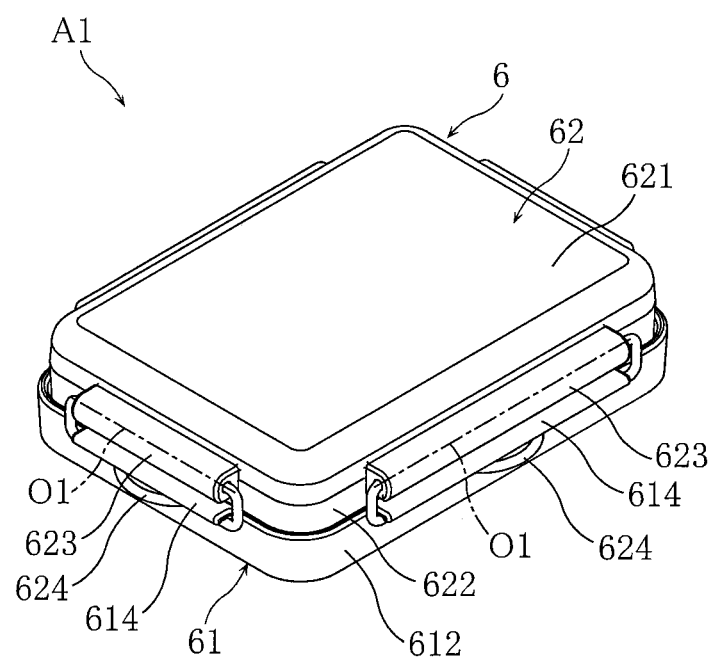
FIG. 1 is a perspective view showing a first embodiment of a culture container transportation set according to the present invention.
Figure 2:
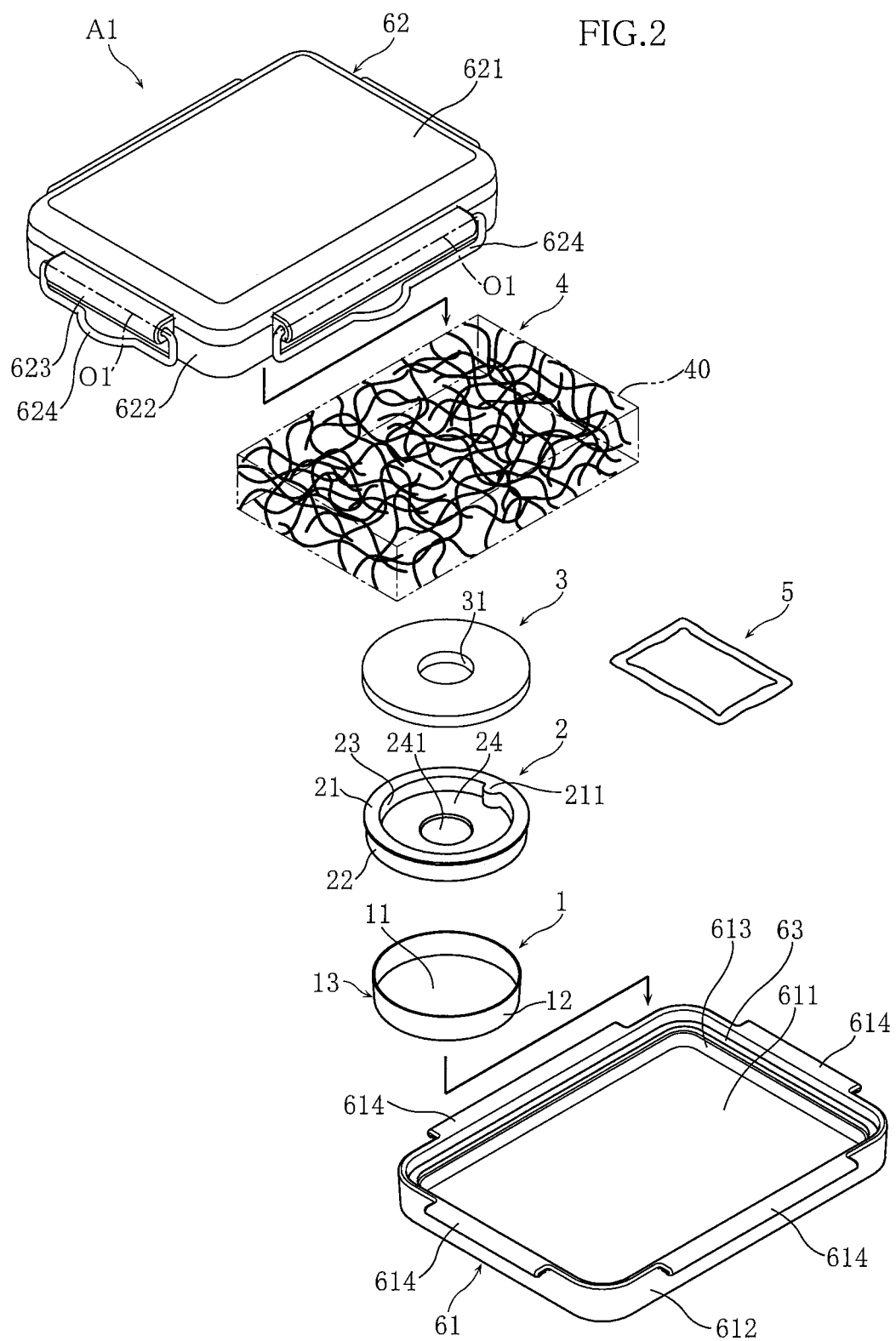
FIG. 2 is an exploded perspective view of the culture container transportation set shown in FIG. 1.
Figure 3:
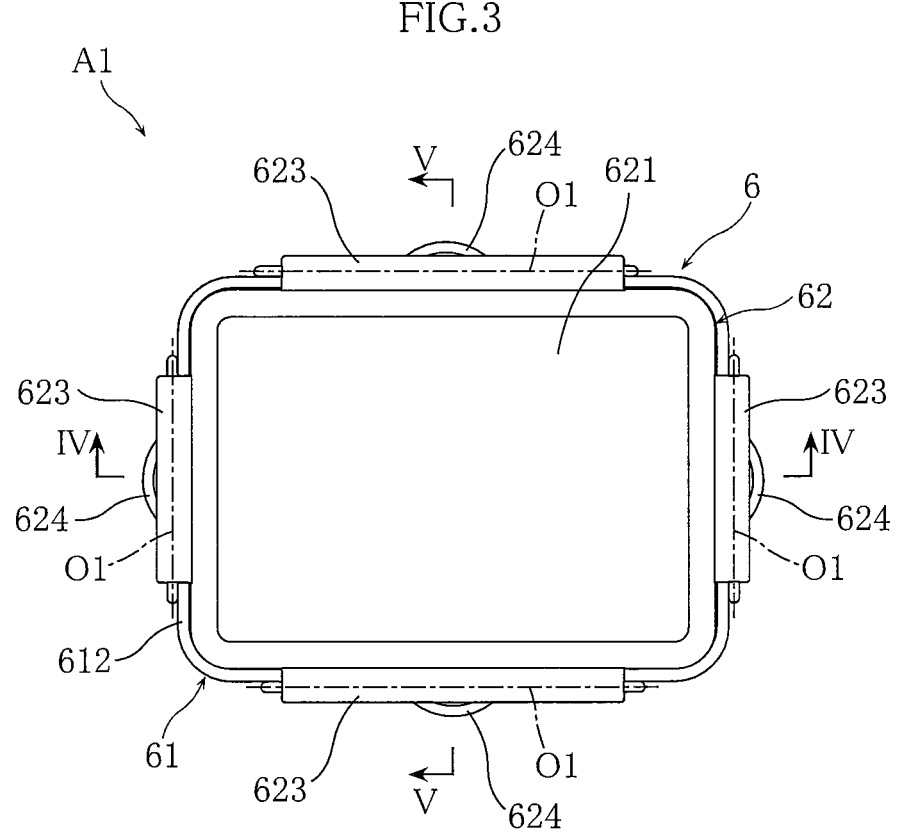
FIG. 3 is a plan view of the culture container transportation set shown in FIG. 1.

FIGS. 1 to 5 show a first embodiment of a culture container transportation set according to the present invention. A culture container transportation set A1 of the present embodiment includes a culture container 1, a cover 2, a pressing member 3, a cushioning material 4, an atmosphere conditioning agent 5, and a housing container 6. FIG. 1 and FIGS. 3 to 5 show an assembled state in which the culture container 1, the cover 2, the pressing member 3, and the cushioning material 4 are stacked, and this will be described more specifically below. FIG. 2 is a perspective view showing the components of the culture container transportation set A1 in a disassembled state.

In the present embodiment, the culture container 1 corresponds to a petri dish (receiver), and includes a vessel 13 made up of a bottom wall 11 and a cylindrical side wall 12 that rises from the peripheral edge of the bottom wall 11. The vessel 13 (culture container 1) is a component for containing cultured cells and a culture medium therein. The culture container 1 is formed of a transparent plastic material, for example. As such a transparent plastic material, a plastic material having transparency is suitable, and examples thereof include, but are not limited to, polystyrene and methylpentene, which are common medical grade plastics, and in addition, cycloolefin polymers and cycloolefin copolymers. It should be noted that, in light of a case where adherent cells are cultured in the vessel 13, hydrophilicity may be imparted, through corona discharge or plasma discharge, to a culture surface (upper surface of the bottom wall 11) to which cells are allowed to adhere, for example.

The cover 2 is a component that is put on the vessel 13 from above to close the opening of the vessel 13. The cover 2 is formed of a flexible and resilient material. Also, the cover 2 is preferably self-adhesive. Examples of the material of the cover 2 include silicone rubber, natural rubber, urethane rubber, and elastomer resin. Among them, silicone rubber is preferable. In light of the contact between the cover 2 and contents (cultured cells and a culture medium) of the culture container 1, it is more preferable that the material of the cover 2 is medical grade silicone rubber, which is free of cytotoxicity and has biocompatibility. Regarding the hardness of the cover 2, it is preferable that the cover 2 has a rubber hardness of about 20 to 40 degrees.

Figure 4:
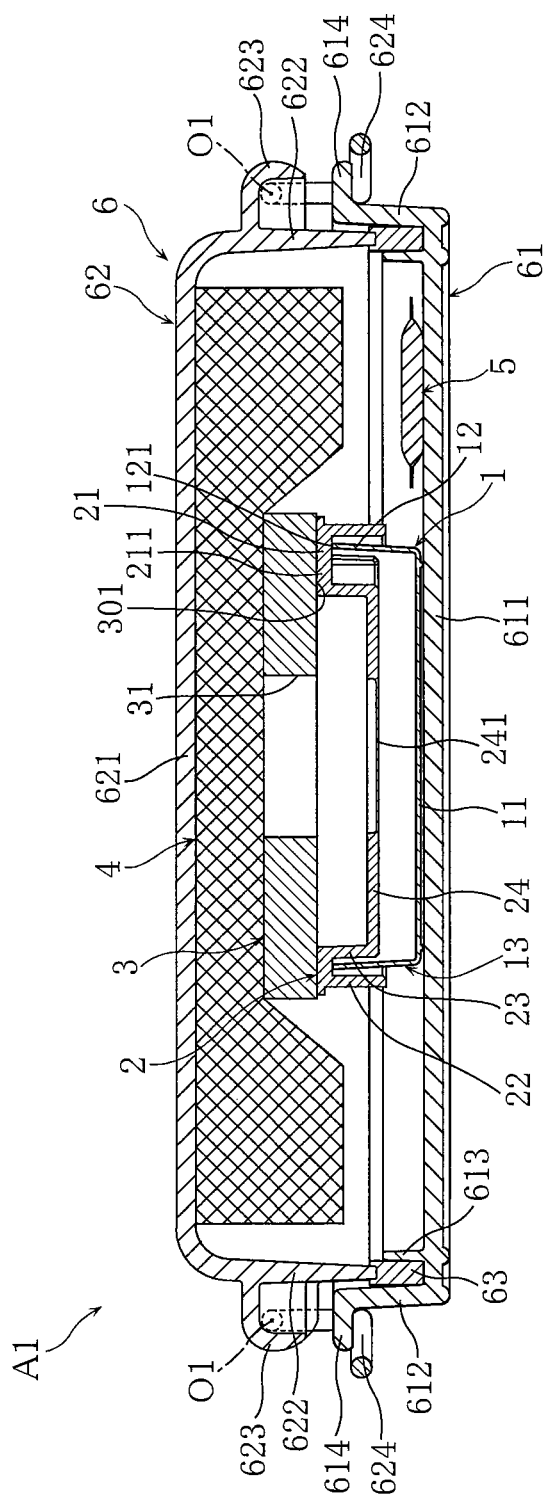
FIG. 4 is a cross-sectional view taken along line IV-IV in FIG. 3.
Figure 5:
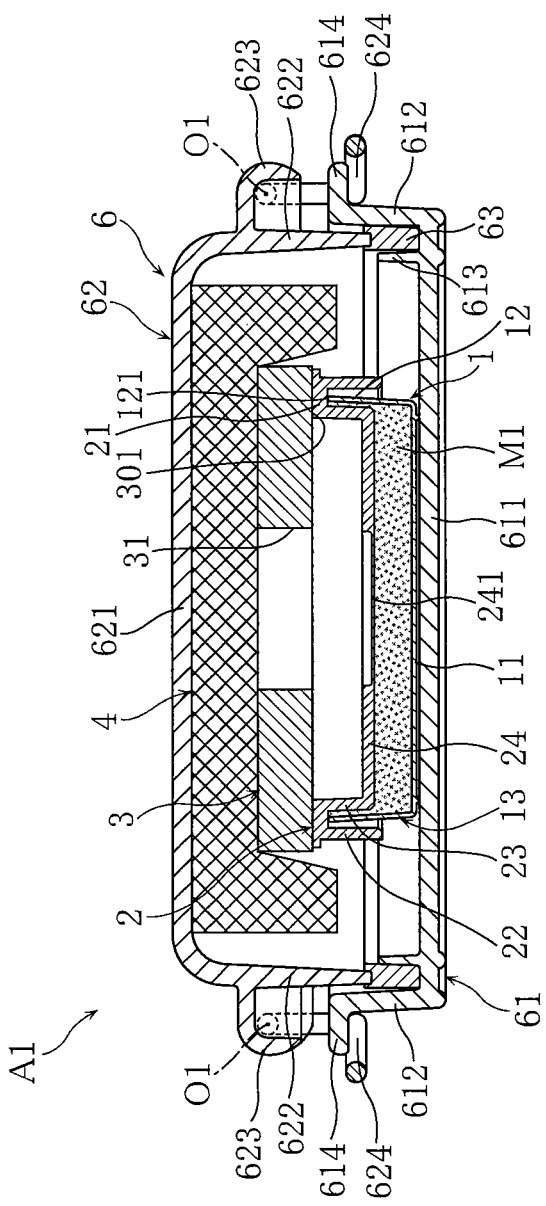
FIG. 5 is a cross-sectional view taken along line V-V in FIG. 3 and shows a state in which contents are in a vessel.

The cover 2 is a rubber molded product, for example, and as shown in FIGS. 2, 4, and 5, the cover 2 has an annular portion 21 having a flat plate shape, an outer cylindrical portion 22 extending downward from the outer peripheral portion of the annular portion 21, an inner cylindrical portion 23 extending downward from the inner peripheral edge of the annular portion 21, and a bottom portion 24 that closes the lower end of the inner cylindrical portion 23.

The annular portion 21 is arranged so as to span across the side wall 12 from the outside to the inside thereof in the radial direction while being in intimate contact with an upper edge portion 121 of the side wall 12. The annular portion has an appropriate thickness and appropriate elastic resilience against loads applied from above and below. The annular portion 21 has a thickness of about 1 to 3 mm, for example. The annular portion 21 corresponds to the thick portion of the present invention. Since the annular portion 21 has an appropriate thickness and elastic resilience, the annular portion 21 has resealing properties with which a hole formed by piercing the annular portion 21 with an injection needle is closed. In the present embodiment, a portion of the annular portion 21 overhangs radially inward to form an overhanging portion 211.

As shown in FIGS. 4 and 5, the inner cylindrical portion 23 and the bottom portion 24 are accommodated inside the side wall 12 of the vessel 13 and protrude in the vertical direction toward the bottom wall 11 of the vessel 13. The inner cylindrical portion 23 and the bottom portion 24 correspond to the protruding portion of the present invention.

As shown in FIGS. 4 and 5, in the present embodiment, the bottom portion 24 has a thin portion 241 provided in a central portion thereof. The thin portion 241 has a smaller thickness than other portions and is in the form of a piece of film. The thin portion 241 has a thickness of about 0.2 to 0.3 mm. This thin portion 241 is gas-permeable. When viewed in the vertical direction, the thin portion 241 is surrounded by the annular portion 21.

As shown in FIGS. 4 and 5, the pressing member 3 is provided on the cover 2. The pressing member 3 is made of a hard synthetic resin material such as polyvinyl chloride, polypropylene, polyethylene, or polystyrene, for example. In the present embodiment, the pressing member 3 has a flat plate shape with a uniform thickness, and its outer shape is circular. The pressing member 3 has a through hole 31 that passes through the pressing member 3 in the thickness direction (vertical direction) at a central portion in the radial direction. This through hole 31 is located inside the side wall 12 as viewed in the vertical direction, and is open toward the thin portion 241 of the cover 2.

As is clear from FIGS. 4 and 5, the lower surface 301 of the pressing member 3 is made flat. In the assembled state, the annular portion 21 of the cover 2 is in intimate contact with the lower surface 301 of the pressing member 3.

The cushioning material 4 shown in FIG. 2 has shape restorability. The cushioning material 4 is a net body having a three-dimensional structure, for example. The net body having a three-dimensional structure has a configuration in which a large number of filaments made of a thermoplastic elastomeric resin are bent in a random manner and contact portions where the above-described filaments are in contact with each other are fused, for example. As shown in FIG. 2, the cushioning material 4 is formed so as to occupy a space delimited into a generally rectangular parallelepiped shape (indicated by virtual lines in FIG. 2; referred to as "cushioning material forming space 40" hereinafter) under natural conditions. The volume occupied by the cushioning material 4 in the cushioning material forming space 40 is relatively small. The cushioning material forming space 40 has a thickness dimension of about 20 to 30 mm, for example.

When a load from the outside is applied, the cushioning material 4 is compressed, and elastic resilience is generated. Then when the load from the outside is released, the cushioning material 4 returns to the original state under natural conditions. In a case where the cushioning material 4 is compressed in the thickness direction of the cushioning material forming space 40, the cushioning material 4 can be compressed to an extent that the dimension in the thickness direction of the cushioning material forming space 40 is reduced to about 25 to 30% (e.g., about 5 to 10 mm).

The housing container 6 is a component for housing the culture container 1, the cover 2, the pressing member 3, the cushioning material 4, and the atmosphere conditioning agent 5 in a sealed state. As shown in FIGS. 2, 4, and 5, the housing container 6 includes a base member 61, a lid body 62, and a packing member 63.

The base member 61 has a bottom plate 611, a side plate 612, a partition plate 613, and locking plates 614. In the present embodiment, the bottom plate 611 has a plate shape with a generally rectangular shape in a plan view. The side plate 612 rises from the outer peripheral edge of the bottom plate 611 and has a substantially rectangular ring shape in a plan view. It should be noted that, as shown in FIGS. 4 and 5, the depth of the base member 61 (i.e., the height dimension of the side plate 612) is set to be substantially the same as or smaller than the height dimension of the culture container 1. The partition plate 613 rises from the bottom plate 611 and has a substantially rectangular ring shape in a plan view. The partition plate 613 is formed at a position away from the side plate 612 by a predetermined distance inside the side plate 612. In the present embodiment, a ring-shaped space surrounded by the bottom plate 611, the side plate 612, and partition plate 613 serves as a space for accommodating the packing member 63 to be described below. The locking plates 614 extend outward from the upper end of the side plate 612, and pivoting portions 624 attached to the lid body 62 to be described below are locked thereto. As shown in FIG. 2 and the like, in the present embodiment, the locking plates 614 are provided at four positions corresponding to the sides of the side plate 612 having a substantially rectangular shape in a plan view.

As shown in FIGS. 2, 4, and 5, the packing member 63 has a substantially rectangular lateral cross section, and has a substantially rectangular ring shape in a plan view. The packing member 63 is formed of a rubber material having predetermined elastic restorability. The packing member 63 is provided in a ring-shaped space surrounded by the bottom plate 611, the side plate 612, and the partition plate 613 in the base member 61.

The lid body 62 is a component for closing the opening of the base member 61, and has a ceiling plate 621, a side plate 622, supporting portions 623, and pivoting portions 624. The ceiling plate 621 has a plate shape with a generally rectangular shape in a plan view. The side plate 612 extends downward from the outer peripheral edge of the bottom plate 611, and has a substantially rectangular ring shape in a plan view. The side plate 612 may overlap the entirety of the packing member 63 provided on the base member 61 in a plan view.

The supporting portions 623 pivotably support the pivoting portions 624, and are provided on the outer surface of the side plate 622. In the present embodiment, the supporting portions 623 are provided at four positions corresponding to the sides of the side plate 622 having a substantially rectangular shape in a plan view.

The pivoting portions 624 are attached to the supporting portions 623 and are pivotable around predetermined pivot axes O1. The pivoting portions 624 are formed by bending metal wire rods, for example. The pivoting portions 624 are attached to four positions corresponding to the supporting portions 623. It should be noted that each of the above-described base member 61 and the lid body 62 is formed in one piece using a relatively hard synthetic resin material, for example.

As is clear from FIGS. 4 and 5, the housing container 6 having the above-described configuration can house the culture container 1, the cover 2, the pressing member 3, and the cushioning material 4 in an assembled state in which these components are stacked. In this assembled state, the multiple pivoting portions 624 provided on the lid body 62 are locked to the locking plates 614 provided on the base member 61. At this time, the packing member 63 is sandwiched between the base member 61 and the lid body 62 and thus compressed, and the lid body 62 (ceiling plate 621) is biased upward due to the elastic resilience of the packing member 63. Here, the space inside the housing container 6 is sealed off from the outside. In the state shown in FIGS. 4 and 5, the distance between the upper surface of the bottom plate 611 and the lower surface of the ceiling plate 621 is constant, and relative movement between the base member 61 and the lid body 62 is prevented. In the present embodiment, the locking plates 614 and the pivoting portions 624 can be used to attach the lid body 62 to the base member 61 in a sealed state, and the clearance between the bottom plate 611 and the ceiling plate 621 is fixed during the attachment. The locking plates 614 and the pivoting portions 624 serve as the locking device of the present invention. It should be noted that the configuration of the locking device is not limited thereto. For example, instead of the pivoting portions 624 formed of metal wire rods, a configuration may be employed in which hinge portions that are connected to the lid body via thin portions are formed in one piece with the lid body and are pivotable around the thin portions serving as pivot axes.

In the housing container 6 shown in FIGS. 4 and 5, the distance between the upper surface of the bottom plate 611 and the lower surface of the ceiling plate 621 is set to be smaller than the height dimension of a stack obtained by merely stacking the culture container 1, the cover 2, the pressing member 3, and the cushioning material 4. When the culture container 1, the cover 2, the pressing member 3, and the cushioning material 4 are merely stacked on the bottom plate 611 (base member 61), and then the lid body 62 is put on and pressed against the resulting stack and is attached to the base member 61, the cushioning material 4 is compressed and deformed as shown in FIGS. 4, 5, and the like. Here, the culture container 1, the cover 2, and the pressing member 3 in the stack are pressed against one another in the height direction due to the elastic resilience of the cushioning material 4. At this time, the culture container 1, the cover 2, the pressing member 3, and the cushioning material 4 are in an assembled state in which they are stacked, and are pressed against one another from above and below by the bottom plate 611 (base member 61) and the ceiling plate 621 (lid body 62), whereby they are integrally held by the housing container 6.

The atmosphere conditioning agent 5 is used to adjust the concentration of a predetermined gas component of the gas in the space inside the housing container 6. The atmosphere conditioning agent 5 contains ascorbic acids, for example, and can adjust an oxygen concentration and a carbon dioxide concentration. The atmosphere conditioning agent 5 is encapsulated in a bag before use. After the bag is open, the atmosphere conditioning agent 5 is placed in the housing container 6, thus making it possible to adjust a gas concentration in the housing container 6. Regarding the gas concentration in the housing container 6, the atmosphere conditioning agent 5 is used to adjust the oxygen concentration to about 5 to 10 vol % and the carbon dioxide concentration to about 5 to 10 vol %. When the atmosphere conditioning agent 5 is used, the oxygen concentration and the carbon dioxide concentration may vary depending on the volume of the space inside the housing container 6.

Next, usage and functions of the culture container transportation set A1 will be described.

The culture container transportation unit A1 is used for placing cultured cells or a biological tissue in the culture container 1 (vessel 13) together with a culture medium and transporting the cultured cells or the biological tissue while maintaining the cultured state (cultured state-maintaining transportation). The cells, biological tissue, and culture medium to be contained in the vessel 13 are not particularly limited.

When adherent cells such as iPS cells are used as the cultured cells, for example, the adherent cells proliferate while adhering to the culture surface (the upper surface of the bottom wall 11) covered with the required amount of a culture medium. During the cultured state-maintaining transportation of the adherent cells, in order to prevent the culture medium from being shaken and the cells adhering to the bottom wall 11 from detaching, it is necessary to completely fill the vessel 13 with the culture medium to restrict the movement of the culture medium.

Figure 6:
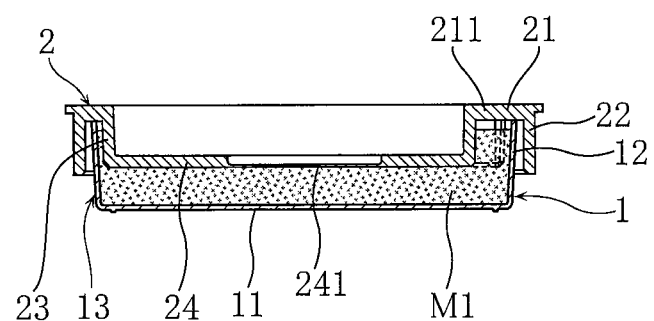
FIG. 6 is a cross-sectional view for explaining a procedure for placing a culture medium in the vessel.
Figure 7:
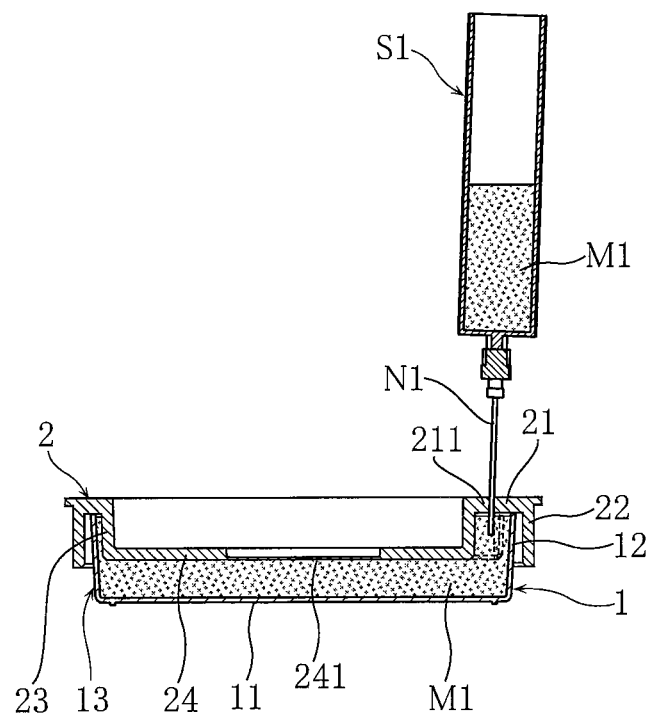
FIG. 7 is a cross-sectional view for explaining the procedure for placing a culture medium in the vessel.

An example of a procedure of placing a culture medium in the vessel 13 will be described with reference to FIGS. 6 and 7. First, as shown in FIG. 6, an appropriate amount of a culture medium M1 is placed in the vessel 13, and the cover 2 is put thereon. Here, the protruding portion (the inner cylindrical portion 23 and the bottom portion 24) of the cover 2 comes into contact with the culture medium and moves further downward, and thus the liquid surface of the culture medium M1 is located slightly below the upper end of the side wall 12. As a result, in the vessel 13, a small air gap remains in an accommodation space covered by the cover 2. Next, as shown in FIG. 7, a syringe S1 is used to inject the culture medium M1 into the above-described accommodation space. The culture medium M1 is injected by piercing the annular portion 21 (overhanging portion 211) with an injection needle N1.

Thereafter, the pressing member 3 and the cushioning material 4 are put thereon, and the culture container 1, the cover 2, the pressing member 3, and the cushioning material 4 are placed in the housing container 6. Accordingly, during cultured state-maintaining transportation, the vessel 13 is filled with the culture medium M1 as shown in FIG. 5. Here, the culture container 1, the cover 2, the pressing member 3, and the cushioning material 4 are pressed from above and below and held in the assembled state by the housing container 6 (the base member 61 and the lid body 62). With this configuration, the contents (the cultured cells and the culture medium) of the vessel 13 are sealed by the cover 2 in a liquid-tight manner. Accordingly, spilling of the contents due to vibrations and the like is prevented during cultured state-maintaining transportation.

With the cover 2 of the present embodiment, the inner cylindrical portion 23 and the bottom portion 24 protrude toward the bottom wall 11 inside the side wall 12. This configuration reduces the volume of the space for accommodating a culture medium and the like in the vessel 13. Therefore, it is possible to reduce the amount of the culture medium M1 to be used in cultured state-maintaining transportation.

As described above, the annular portion 21 of the cover 2 has resealing properties with which a hole formed by piercing the annular portion 21 with the injection needle N1 is closed. Moreover, in the assembled state, the annular portion 21 is in intimate contact with the lower surface 301 of the pressing member 3. Accordingly, during transportation of the culture container transportation set A1, the contents (the culture medium and the like) do not leak from the above-described hole formed through piercing.

The annular portion 21 of the cover 2 is in intimate contact with the upper edge portion 121 of the side wall 12. Moreover, the cover 2 has the gas-permeable thin portion 241. The above-described thin portion 241 is surrounded by the annular portion 21 as viewed in the vertical direction. Thus, the contents of the vessel 13 remain in communication with the atmosphere outside the vessel 13 in the space inside the housing container 6. Therefore, with the present embodiment, it is possible to culture the contents of the vessel 13 under ventilated conditions during transportation.

The pressing member 3 is provided with the through hole 31 that is located inside the side wall 12 as viewed in the vertical direction. With this configuration, the thin portion 241 is not blocked by the pressing member 3 provided on the cover 2. Therefore, this configuration is suitable for ensuring that the vessel 13 is in communication with the atmosphere outside the vessel 13.

The culture container transportation set A1 of the present embodiment includes the atmosphere conditioning agent 5 with which a gas concentration inside the housing container 6 can be adjusted. With this configuration, it is possible to perform cultured state-maintaining transportation under a predetermined gas environment while the vessel 13 remains in communication with the atmosphere outside the vessel 13 (in the space inside the housing container 6).

In the present embodiment, the cushioning material 4 is a net body having a three-dimensional structure, and the volume occupied by the cushioning material 4 is relatively small. With the cushioning material 4 having this configuration, the weight thereof is small relative to the size (volume) of the above-described cushioning material forming space 40, thus making it possible to reduce the weight of the cushioning material 4. In the case where the atmosphere conditioning agent is used to adjust a gas concentration inside the housing container 6, since the volume occupied by the cushioning material 4 is small, it is possible to reduce the influence of the space occupied by the cushioning material 4 on a gas concentration inside the housing container 6.

The housing container 6 includes the base member 61, the lid body 62, and the packing member 63, and relative movement between the base member 61 and the lid body 62 is prevented in the state in which the packing member 63 is sandwiched between the base member 61 and the lid body 62. With this configuration, the distance between the bottom plate 611 of the base member 61 and the ceiling plate 621 of the lid body 62 can be fixed to a constant value. Therefore, when the culture container 1, the cover 2, the pressing member 3, and the cushioning material 4 are assembled together and placed in the housing container 6, the culture container 1, the cover 2, the pressing member 3, and the cushioning material 4 are held by the housing container 6 with a constant pressing force, and the state of being pressed by the housing container 6 is thus stabilized.

After the culture container transportation set A1 has been transported, the culture container 1, the cover 2, the pressing member 3, and the cushioning material 4 can be easily disassembled by releasing the locking of the pivoting portions 624 to the locking plates 614 on the housing container 6 and removing the lid body 62 from the base member 61. That is, in the assembled state, the culture container 1, the cover 2, the pressing member 3, and the cushioning material 4 are merely stacked, and therefore, the cushioning material 4, the pressing member 3, and the cover 2 can be smoothly removed in this order from the top. Accordingly, it is possible to prevent an issue where the contents of the culture container 1 (vessel 13) spill out when removing the cover 2 from the culture container 1.

Figure 8:
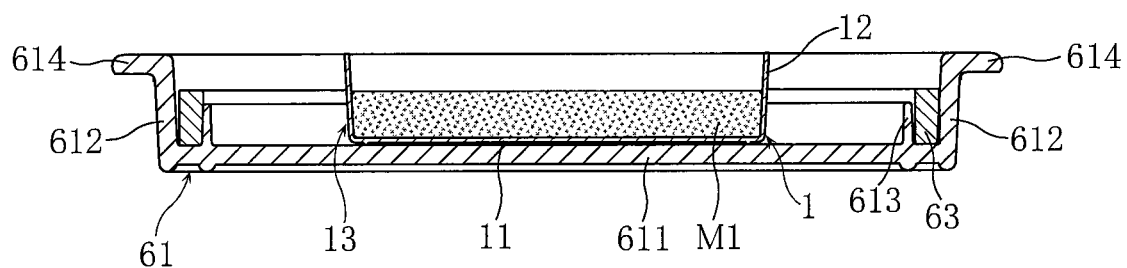
FIG. 8 is a cross-sectional view for explaining usage of the culture container transportation set shown in FIG. 1.

In the present embodiment, the depth of the base member 61 (i.e., the height dimension of the side plate 612) is set to be substantially the same as or smaller than the height dimension of the culture container 1. With this configuration, when the culture container 1 placed on the bottom plate 611 of the base member 61 as shown in FIG. 8 is removed, it is easy to lift the culture container 1 by holding the side wall 12 of the culture container 1. Therefore, it is possible to prevent an issue where the contents of the culture container 1 (vessel 13) spill out when removing the culture container 1 from the housing container 6.

FIGS. 9 to 12 show a second embodiment of the culture container transportation set according to the present invention. It should be noted that, in FIG. 9 and the subsequent drawings, components that are identical or similar to those of the above-described embodiment are denoted by the same reference numerals as those used in the above-described embodiment, and the descriptions thereof may be omitted as appropriate.

Figure 9:
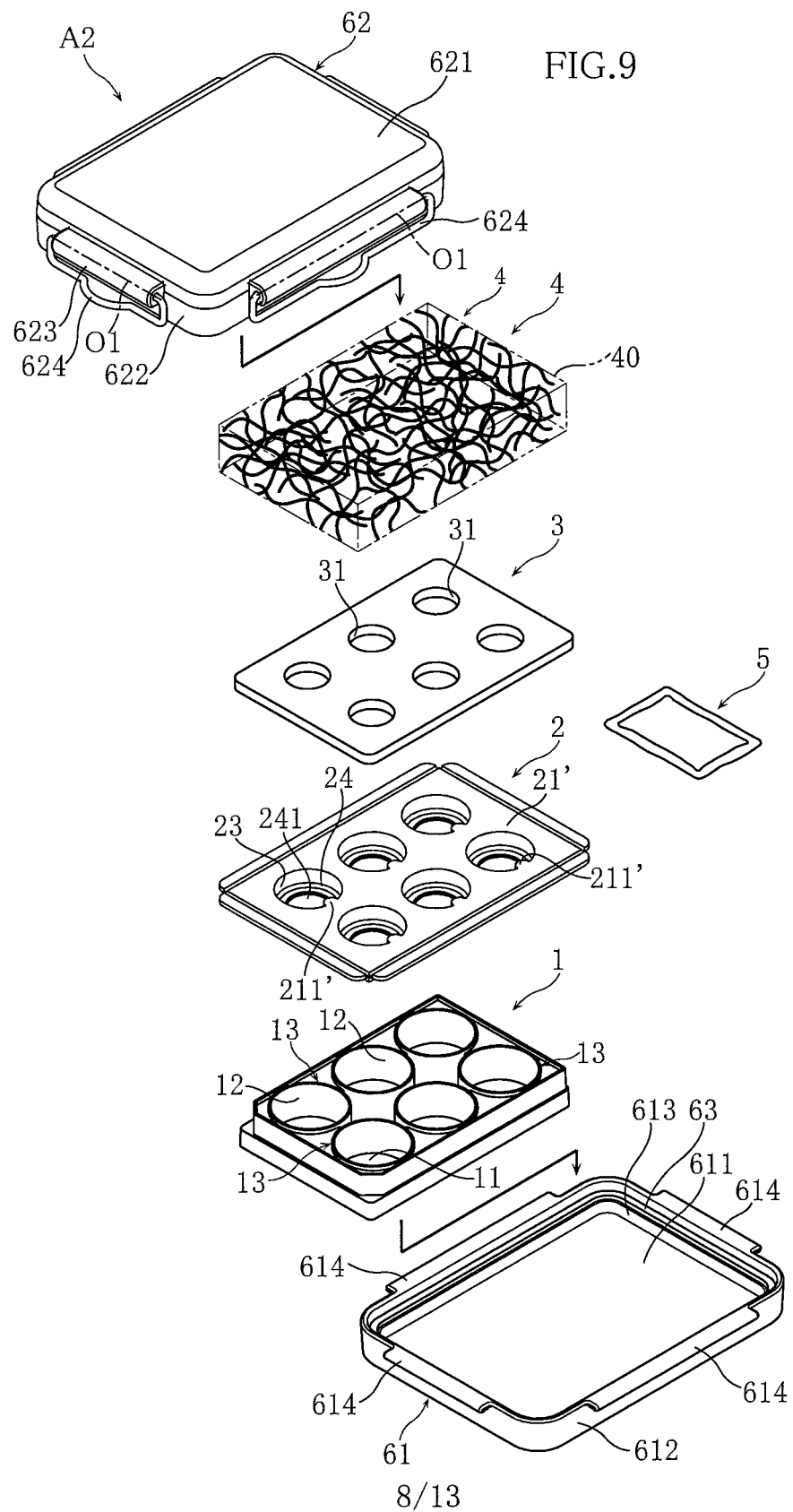
FIG. 9 is an exploded perspective view showing a second embodiment of the culture container transportation set according to the present invention.
Figure 10:
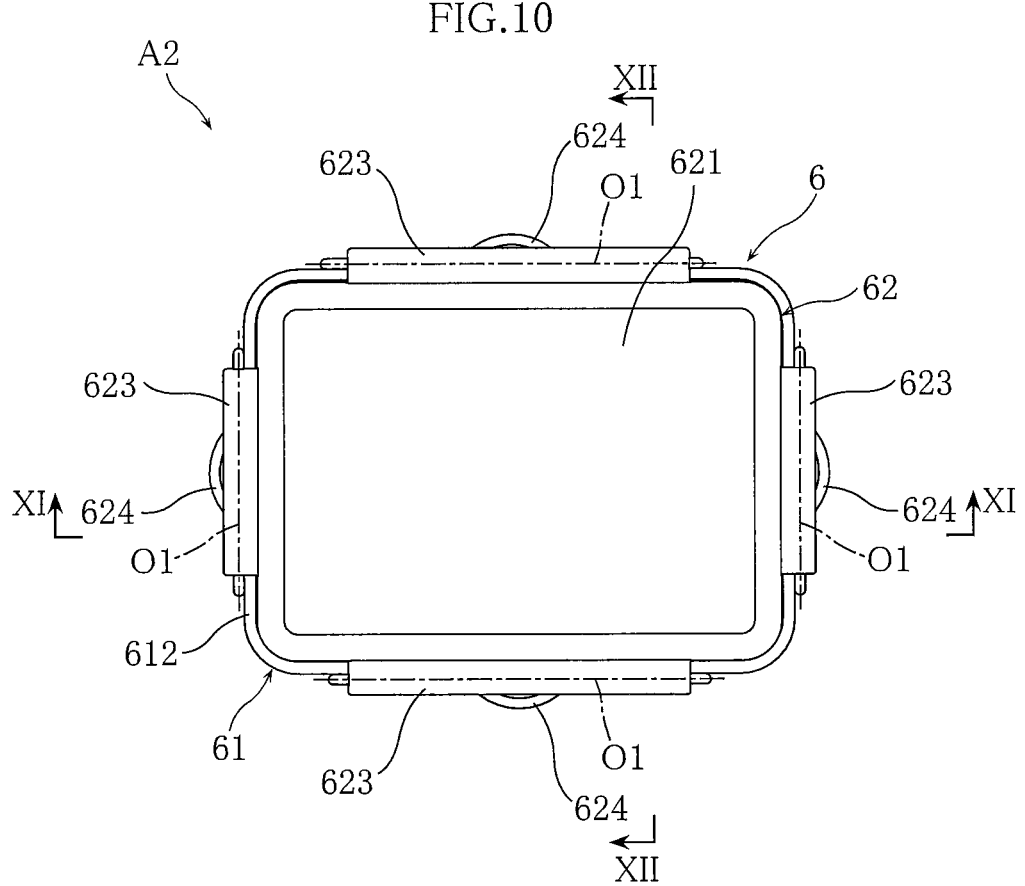
FIG. 10 is a plan view of the culture container transportation set shown in FIG. 9.
Figure 11:
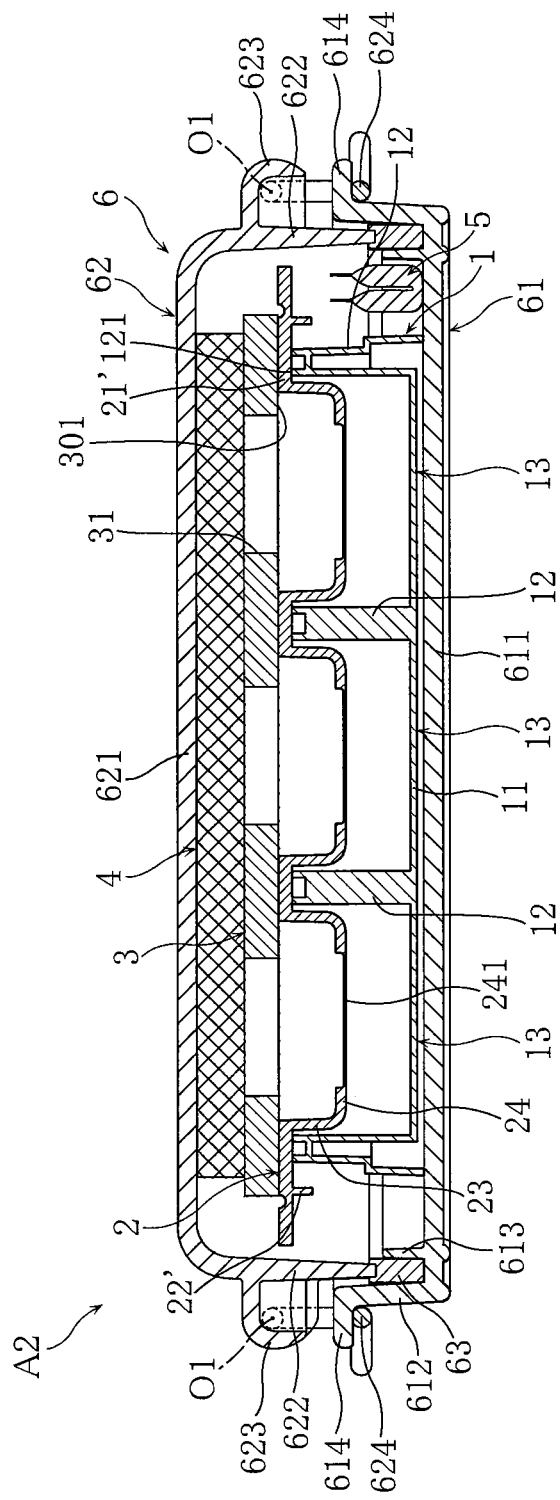
FIG. 11 is a cross-sectional view taken along line XI-XI in FIG. 10.
Figure 12:
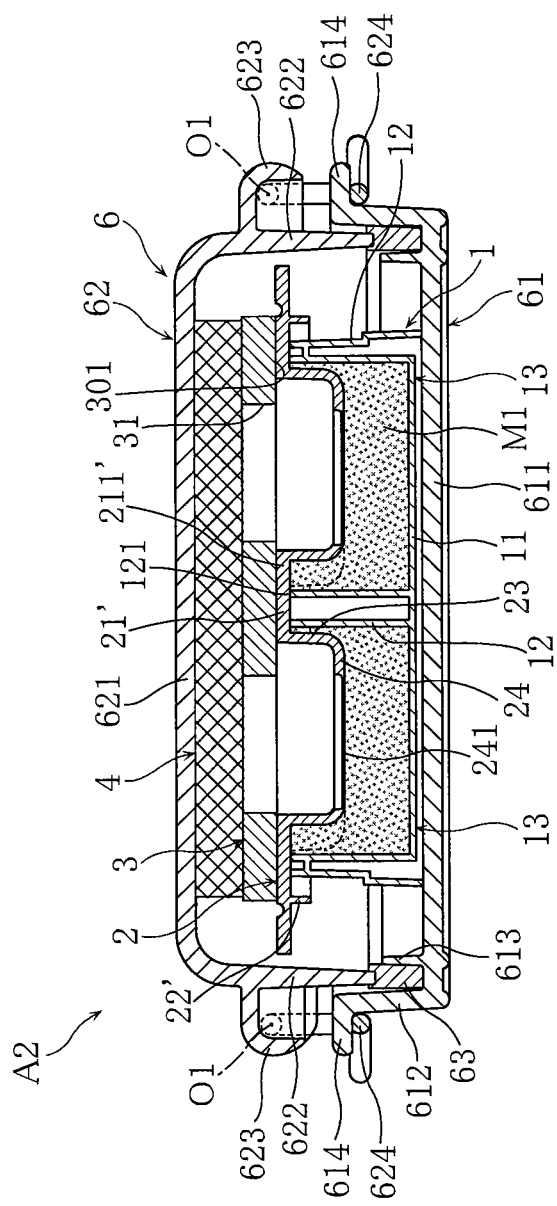
FIG. 12 is a cross-sectional view taken along line XII-XII in FIG. 10 and shows a state in which contents are in a vessel.

A culture container transportation set A2 shown in FIG. 9 includes a culture container 1, a cover 2, a pressing member 3, a cushioning material 4, an atmosphere conditioning agent 5, and a housing container 6. FIGS. 10 to 12 show an assembled state in which the culture container 1, the cover 2, the pressing member 3, and the cushioning material 4 are stacked. FIG. 9 is a perspective view showing the components of the culture container transportation set A2 in a disassembled state. In the present embodiment, the culture container 1 corresponds to a so-called well plate, and includes multiple (six in the present embodiment) wells serving as the vessels 13. Each of the multiple vessels 13 is configured by an elongated rectangular bottom wall 11 that is shared between the vessels 13, and a cylindrical side wall 12 that rises from an appropriate position on the bottom wall 11.

The cover 2 is a rubber molded product, for example, and as shown in FIGS. 9, 11, and 12, the cover 2 has a generally elongated rectangular flat plate portion 21', an outer tubular portion 22' extending downward from the outer peripheral portion of the flat plate portion 21', multiple inner cylindrical portions 23, and multiple bottom portions 24.

The flat plate portion 21' is arranged so as to span across the respective side walls 12 from the outside to the inside thereof in the radial direction while being in intimate contact with upper edge portions 121 of the side walls 12. The flat plate portion 21' has an appropriate thickness and appropriate elastic resilience against the loads applied from above and below. The flat plate portion 21' has a thickness of about 1 to 3 mm, for example. The flat plate portion 21' corresponds to the thick portion of the present invention. Since the flat plate portion 21' has an appropriate thickness and elastic resilience, the flat plate portion 21' has resealing properties with which a hole formed by piercing the flat plate portion 21' with an injection needle is closed. In the present embodiment, portions of the flat plate portion 21' overhang radially inward from the inner cylindrical portions 23 to form overhanging portions 211'.

As shown in FIGS. 11 and 12, the inner cylindrical portions 23 and the bottom portions 24 are accommodated inside the side walls 12 of the vessels 13 and protrude in the vertical direction toward the bottom wall 11 of the vessels 13. The inner cylindrical portions 23 and the bottom portions 24 correspond to the protruding portions of the present invention.

As shown in FIGS. 11 and 12, in the present embodiment, each of the bottom portions 24 has a thin portion 241 provided in a central portion thereof. The thin portion 241 is in the form of a piece of film and is gas-permeable. When viewed in the vertical direction, each of the thin portions 241 is surrounded by the flat plate portion 21'.

As shown in FIGS. 11 and 12, the pressing member 3 is provided on the cover 2. In the present embodiment, the pressing member 3 has a flat plate shape with a uniform thickness, and its outer shape is substantially rectangular. The pressing member 3 has multiple through holes 31 that pass through the pressing member 3 in the thickness direction (vertical direction) at appropriate positions. These through holes 31 are located inside the respective side walls 12 as viewed in the vertical direction, and are open toward the thin portions 241 of the cover 2.

As is clear from FIGS. 11 and 12, the lower surface 301 of the pressing member 3 is made flat. In the assembled state, the flat plate portion 21' of the cover 2 is in intimate contact with the lower surface 301 of the pressing member 3.

The cushioning material 4, the housing container 6, and the atmosphere conditioning agent 5 are substantially the same as those of the above-described first embodiment, and therefore, descriptions of these components are omitted. It should be noted that, as shown in FIGS. 11 and 12, the depth of the base member 61 (i.e., the height dimension of the side plate 612) in the housing container 6 is set to be smaller than the height dimension of the culture container 1.

As is clear from FIGS. 11 and 12, the housing container 6 can house the culture container 1, the cover 2, the pressing member 3, and the cushioning material 4 in an assembled state in which these components are stacked. In this assembled state, the multiple pivoting portions 624 provided on the lid body 62 are locked to the locking plates 614 provided on the base member 61. At this time, the packing member 63 is sandwiched between the base member 61 and the lid body 62 and thus compressed, and the lid body 62 (ceiling plate 621) is biased upward due to the elastic resilience of the packing member 63. Here, the space inside the housing container 6 is sealed off from the outside. In the state shown in FIGS. 11 and 12, the distance between the upper surface of the bottom plate 611 and the lower surface of the ceiling plate 621 is constant, and relative movement between the base member 61 and the lid body 62 is prevented. In the present embodiment, the locking plates 614 and the pivoting portions 624 can be used to attach the lid body 62 to the base member 61 in a sealed state, and the clearance between the bottom plate 611 and the ceiling plate 621 is fixed during the attachment. The locking plates 614 and the pivoting portions 624 serve as the locking device of the present invention.

In the housing container 6 shown in FIGS. 11 and 12, the distance between the upper surface of the bottom plate 611 and the lower surface of the ceiling plate 621 is set to be smaller than the height dimension of a stack obtained by merely stacking the culture container 1, the cover 2, the pressing member 3, and the cushioning material 4. When the culture container 1, the cover 2, the pressing member 3, and the cushioning material 4 are merely stacked on the bottom plate 611 (base member 61), and then the lid body 62 is put on and pressed against the resulting stack and is attached to the base member 61, the cushioning material 4 is compressed and deformed as shown in FIGS. 11, 12, and the like. Here, the culture container 1, the cover 2, and the pressing member 3 in the stack are pressed against one another in the height direction due to the elastic resilience of the cushioning material 4. At this time, the culture container 1, the cover 2, the pressing member 3, and the cushioning material 4 are in an assembled state in which they are stacked, and are pressed against one another from above and below by the bottom plate 611 (base member 61) and the ceiling plate 621 (lid body 62), whereby they are integrally held by the housing container 6.

Next, usage and functions of the culture container transportation set A2 will be described.

The culture container transportation unit A2 is used for placing cultured cells or a biological tissue in the culture container 1 (vessel 13) together with a culture medium and transporting the cultured cells or the biological tissue while maintaining the cultured state (cultured state-maintaining transportation). The cells, biological tissue, and culture medium to be contained in the vessel 13 are not particularly limited.

When adherent cells such as iPS cells are used as the cultured cells, for example, the adherent cells proliferate while adhering to the culture surface (the upper surface of the bottom wall 11) covered with the required amount of a culture medium. During the cultured state-maintaining transportation of the adherent cells, in order to prevent the culture medium from being shaken and the cells adhering to the bottom wall 11 from detaching, it is necessary to completely fill the vessels 13 with the culture medium to restrict the movement of the culture medium.

A procedure of placing a culture medium in the respective vessels 13 can be performed in the same manner as in the description of the culture container transportation set A1 described with reference to FIGS. 6 and 7. That is, after the cover 2 is put on the vessels 13 in which an appropriate amount of a culture medium has been placed, a syringe is used to inject the culture medium into the accommodation spaces in the vessels 13 covered with the cover 2. The culture medium is injected by piercing the flat plate portion 21' (overhanging portion 211') with an injection needle.

Next, the pressing member 3 and the cushioning material 4 are put thereon, and the culture container 1, the cover 2, the pressing member 3, and the cushioning material 4 are placed in the housing container 6. Accordingly, during cultured state-maintaining transportation, the vessels 13 are filled with the culture medium M1 as shown in FIG. 12. Here, the culture container 1, the cover 2, the pressing member 3, and the cushioning material 4 are pressed from above and below and held in the assembled state by the housing container 6 (the base member 61 and the lid body 62). With this configuration, the contents (the cultured cells and the culture medium) of the vessels 13 are sealed by the cover 2 in a liquid-tight manner. Accordingly, spilling of the contents due to vibrations and the like is prevented during cultured state-maintaining transportation.

With the cover 2 of the present embodiment, the inner cylindrical portions 23 and the bottom portions 24 protrude toward the bottom wall 11 inside the respective side walls 12. This configuration reduces the volume of the space for accommodating a culture medium and the like in each of the vessels 13. Therefore, it is possible to reduce the amount of the culture medium M1 to be used in cultured state-maintaining transportation.

As described above, the flat plate portion 21' of the cover 2 has resealing properties with which a hole formed by piercing the flat plate portion 21' with the injection needle N1 is closed. Moreover, in the assembled state, the flat plate portion 21' is in intimate contact with the lower surface 301 of the pressing member 3. Accordingly, during transportation of the culture container transportation set A2, the contents (the culture medium and the like) do not leak from the above-described hole formed through piercing.

The flat plate portion 21' of the cover 2 is in intimate contact with the upper edge portions 121 of the side walls 12. Moreover, the cover 2 has the gas-permeable thin portions 241. The respective thin portions 241 are surrounded by the flat plate portion 21' as viewed in the vertical direction. Thus, the contents of the vessels 13 remain in communication with the atmosphere outside the vessels 13 in the space inside the housing container 6. Therefore, with the present embodiment, it is possible to culture the contents of the vessels 13 under ventilated conditions during transportation.

The pressing member 3 is provided with the through holes 31 that are located inside the respective side walls 12 as viewed in the vertical direction. With this configuration, the thin portions 241 are not blocked by the pressing member 3 provided on the cover 2. Therefore, this configuration is suitable for ensuring that the vessels 13 are in communication with the atmosphere outside the vessels 13.

The culture container transportation set A2 of the present embodiment includes the atmosphere conditioning agent 5 with which a gas concentration inside the housing container 6 can be adjusted. With this configuration, it is possible to perform cultured state-maintaining transportation under a predetermined gas environment while the vessels 13 remain in communication with the atmosphere outside the vessels 13 (in the space inside the housing container 6).

The cushioning material 4 is a net body having a three-dimensional structure, and the volume occupied by the cushioning material 4 is relatively small. With the cushioning material 4 having this configuration, the weight thereof is small relative to the size (volume) of the above-described cushioning material forming space 40, thus making it possible to reduce the weight of the cushioning material 4. In the case where the atmosphere conditioning agent 5 is used to adjust a gas concentration inside the housing container 6, since the volume occupied by the cushioning material 4 is small, it is possible to reduce the influence of the space occupied by the cushioning material 4 on a gas concentration inside the housing container 6.

The housing container 6 includes the base member 61, the lid body 62, and the packing member 63, and relative movement between the base member 61 and the lid body 62 is prevented in the state in which the packing member 63 is sandwiched between the base member 61 and the lid body 62. With this configuration, the distance between the bottom plate 611 of the base member 61 and the ceiling plate 621 of the lid body 62 can be fixed to a constant value. Therefore, when the culture container 1, the cover 2, the pressing member 3, and the cushioning material 4 are assembled together and placed in the housing container 6, the culture container 1, the cover 2, the pressing member 3, and the cushioning material 4 are held by the housing container 6 with a constant pressing force, and the state of being pressed by the housing container 6 is thus stabilized.

After the culture container transportation set A2 has been transported, the culture container 1, the cover 2, the pressing member 3, and the cushioning material 4 can be easily disassembled by releasing the locking of the pivoting portions 624 to the locking plates 614 on the housing container 6 and removing the lid body 62 from the base member 61. That is, in the assembled state, the culture container 1, the cover 2, the pressing member 3, and the cushioning material 4 are merely stacked, and therefore, the cushioning material 4, the pressing member 3, and the cover 2 can be smoothly removed in this order from the top. Accordingly, it is possible to prevent an issue where the contents of the culture container 1 (vessels 13) spill out when removing the cover 2 from the culture container 1.

Figure 13:
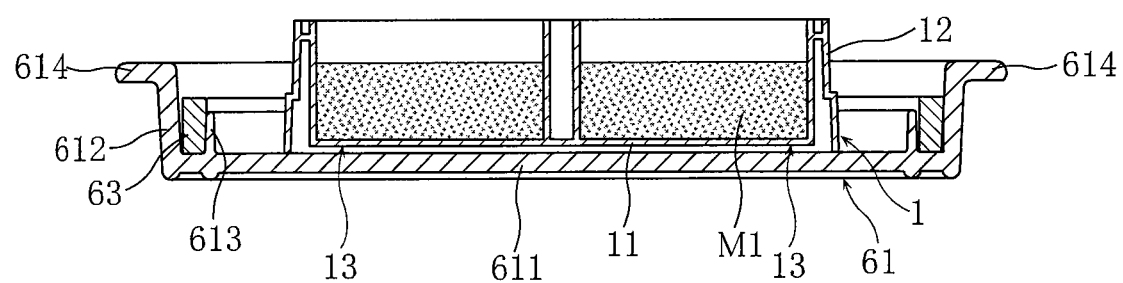
FIG. 13 is a cross-sectional view for explaining usage of the culture container transportation set shown in FIG. 9.

In the present embodiment, the depth of the base member 61 (i.e., the height dimension of the side plate 612) is set to be smaller than the height dimension of the culture container 1. With this configuration, when the culture container 1 placed on the bottom plate 611 of the base member 61 as shown in FIG. 13 is removed, it is easy to lift the culture container 1 by holding the side walls 12 of the culture container 1. Therefore, it is possible to prevent an issue where the contents of the culture container 1 (vessels 13) spill out when removing the culture container 1 from the housing container 6.

Although the embodiments of the present invention have been described above, the scope of the present invention is not limited to the above-described embodiments, and all changes within the scope described in the claims are encompassed in the scope of the present invention.

Although the embodiment in which the cover is made of rubber or elastomer resin is described above, there is no limitation thereto. The cover 2 may also be made of a resin film, for example. The resin film has no definite form and is gas-permeable, and can be formed of polymethylpentene containing olefin or polyvinylidene chloride, for example.

The cover may also be formed of a relatively thick sheet material with a uniform thickness. The sheet material is not gas-permeable, but in the case of a relatively short-period transportation time, it is possible to seal the culture container 1 in a liquid-tight manner using the sheet material, which is inexpensive. Therefore, it is possible to reduce the cost and simplify the structure.

Figure 14:
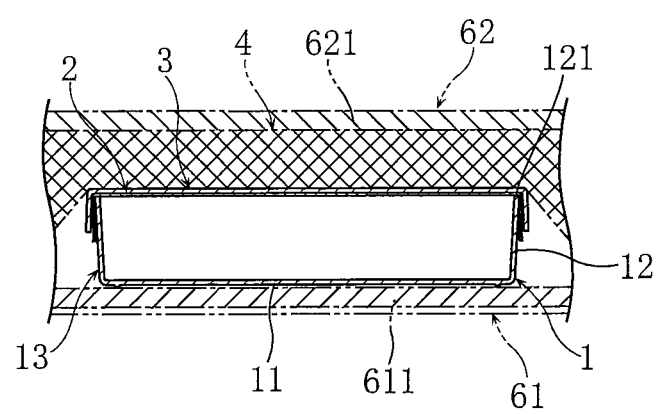
FIG. 14 is a cross-sectional view showing another example of the configuration of a cover and a pressing member.
Figure 15:
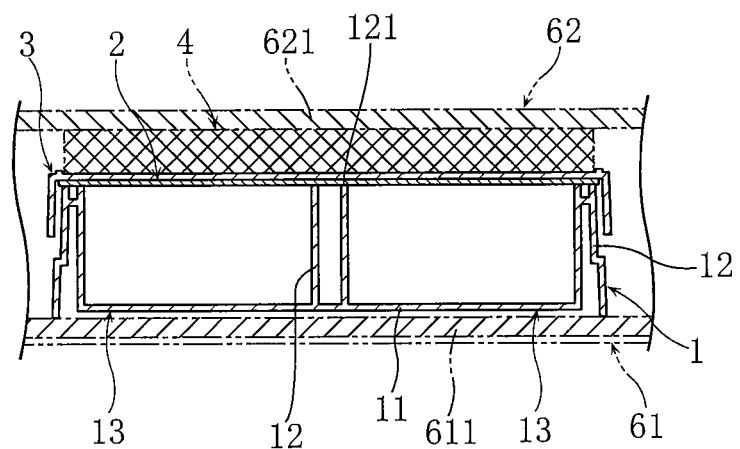
FIG. 15 is a cross-sectional view showing still another example of the configuration of the cover and the pressing member.

It should be noted that, when a sheet material that is not required to be gas-permeable is used as the cover, a lid set in the finished product of the culture container 1 may be used as the pressing member. FIGS. 14 and 15 show examples of such a cover 2 and pressing member 3 having such configurations. FIG. 14 shows a case where a petri dish is used as the culture container 1, and a lid set in the petri dish can be used as the pressing member 3 as it is. FIG. 15 shows a case where a well plate is used as the culture container 1, and a lid set in the well plate can be used as the pressing member 3 as it is.

Figure 16:
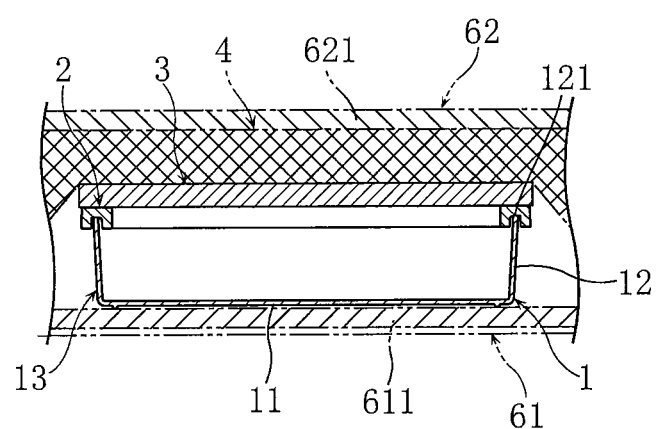
FIG. 16 is a cross-sectional view showing yet another example of the configuration of the cover and the pressing member.

When the atmosphere conditioning agent is not placed inside the housing container, a configuration in which the housing container is not sealed off from the outside may also be employed. Furthermore, the cover may be configured to cover only the upper edge portion 121 of the side wall 12 of the culture container 1. FIG. 16 shows an example of the configuration of the cover 2 having such a configuration. The cover 2 shown in FIG. 16 is formed in an annular shape so as to cover the upper edge portion 121 of the side wall 12 of the culture container 1, and the pressing member 3 is formed in a flat plate shape and covers the cover 2 and the entire opening at the upper end of the culture container 1.

Furthermore, even when the cover is gas-permeable, a container that is not sealable may be used as the housing container. When the housing container is in communication with the outside atmosphere, the culture container 1 can be transported in a state in which culturing is performed under an atmospheric environment.

Although the case where the cushioning material 4 is provided between the pressing member 3 and the housing container (lid body 62) is described in the above-described embodiment, the cushioning material 4 may also be provided between the housing container 6 (base member 61) and the culture container 1. Moreover, the degree of compression of the cushioning material 4 may be adjusted using a means such as stacking an additional plate material on the cushioning material 4, for example.

It should be noted that, during cultured state-maintaining transportation performed using the culture container transportation set of the present invention, contents (cultured cells or a biological tissue together with a culture medium) are placed in the vessel of the culture container. A unit (cell and biological tissue transportation unit) including the culture container transportation set in which the contents are placed also falls within the scope of the present invention.

The invention claimed is:

1. A culture container transportation set comprising:
a culture container including at least one vessel comprising a bottom wall and a tubular side wall that rises from the bottom wall;
a flexible cover that covers an upper edge portion of the side wall of the vessel, comprising:
a flat annular portion having a lower surface in direct contact with an upper edge of the vessel side wall; and
a closing portion extending from the annular portion at a position inside the vessel side wall in plan view, the closing portion, together with the annular portion, being configured to close an opening defined by the upper edge of the vessel side wall;
a hard pressing member provided on the cover;
a cushioning material having shape restorability; and
a housing container comprising:
a base member with a housing portion comprising a bottom plate and a side wall rising from the bottom plate and defining an opening;
a lid body for closing the opening of the housing portion, comprising a ceiling plate and a side wall extending downward from the ceiling plate;
a ring-shaped packing member formed of a flexible material sandwiched between the base member and lid body; and
a locking device that, when locked, prevents relative movement between the base member and the lid body with the packing member sandwiched between the base member and the lid body,
the housing container providing a sealed inner space containing an assembly of the culture container, the cover, the pressing member and the cushioning material stacked on one another in a direction perpendicular to the bottom plate of the base member, with the assembly spaced from inner surfaces of the side wall of the base member and the side wall of the lid, the assembly being pressed from above and below by the bottom plate of the base member and the ceiling plate of the lid,
wherein the cushioning material is provided between the bottom plate of the base member and the culture container or between the pressing member and the ceiling plate of the lid.

2. The culture container transportation set according to claim 1, wherein the cover comprises a gas-permeable portion at a position located inside the side wall as viewed in a vertical direction.

3. The culture container transportation set according to claim 2, wherein the cover includes: a thick portion that is in intimate contact with the upper edge portion of the side wall and has a relatively large thickness; and a gas-permeable thin portion that is surrounded by the thick portion as viewed in the vertical direction and has a relatively small thickness.

4. The culture container transportation set according to claim 3, wherein the thick portion has resealing properties with which a hole formed by piercing the thick portion with an injection needle is closed, and is in intimate contact with a lower surface of the pressing member in the assembly.

5. The culture container transportation set according to claim 1, wherein the closing portion of the cover includes a protruding portion that is accommodated inside the side wall and protrudes toward the bottom wall.

6. The culture container transportation set according to claim 1, wherein the cover is formed of a gas-permeable film.

7. The culture container transportation set according to claim 1, wherein the pressing member includes a tubular portion that is accommodated inside the side wall and extends downward toward the bottom wall.

8. The culture container transportation set according to claim 1, wherein the pressing member is formed with a through hole that is located inside the side wall as viewed in the vertical direction and passes through the pressing member in the vertical direction.

9. The culture container transportation set according to claim 1, further comprising an atmosphere conditioning agent that adjusts a gas concentration inside the housing container.

10. The culture container transportation set according to claim 9, wherein the atmosphere conditioning agent contains ascorbic acids and adjusts an oxygen concentration and a carbon dioxide concentration.

11. The culture container transportation set according to claim 1, wherein the cushioning material is a net body.

12. The culture container transportation set according to claim 1, wherein the pressing member is held in direct contact with the annular portion of the cover, and
the cushioning material is provided between the pressing member and the ceiling plate of the housing container and held in direct contact with the pressing member and the ceiling plate of the housing container.

13. The culture container transportation set according to claim 5, wherein the protruding portion comprises:
an inner cylindrical portion extending downward from the annular portion at a position inside the vessel side wall; and
a bottom portion extending inwardly from the inner cylindrical portion at a position below the upper edge of the vessel side wall to close an opening defined by the inner cylindrical portion.

14. The culture container transportation set according to claim 1, wherein the cover includes an outer cylindrical portion extending downward from the annular portion at a position outside the vessel side wall.

15. A cell and biological tissue transportation unit comprising:
a culture container transportation set according to claim 1; and
cells or biological tissues placed in the vessel of the culture container transportation set together with a culture medium.

* * * * *